United States Patent [19]
Herskowitz

[11] Patent Number: 5,554,123
[45] Date of Patent: Sep. 10, 1996

[54] PORTABLE INFUSION PUMP

[76] Inventor: Glenn Herskowitz, 220 Hawthorne Ave., Larkspur, Calif. 94939

[21] Appl. No.: 331,883

[22] Filed: Oct. 31, 1994

[51] Int. Cl.$^6$ .......................... A61M 5/155; A61M 5/145
[52] U.S. Cl. ........................................ 604/141; 604/143
[58] Field of Search .................................. 604/141, 143, 604/153, 131, 411, 412, 413, 414

[56] References Cited

U.S. PATENT DOCUMENTS

| | | |
|---|---|---|
| 1,986,484 | 1/1935 | Schueler . |
| 2,898,917 | 8/1959 | Wallace . |
| 3,329,390 | 7/1967 | Hulsey . |
| 3,366,363 | 1/1968 | Hogan et al. . |
| 3,487,837 | 1/1970 | Petersen . |
| 3,565,078 | 2/1971 | Vailancourt . |
| 3,620,500 | 11/1971 | Santomierl . |
| 3,703,899 | 11/1972 | Calinog . |
| 3,853,127 | 12/1974 | Spademan . |
| 3,895,741 | 7/1975 | Nugent ...................................... 604/141 |
| 3,970,089 | 7/1976 | Saice . |
| 3,977,400 | 8/1976 | Moorehead . |
| 3,994,287 | 11/1976 | Turp et al. . |
| 4,000,739 | 1/1977 | Stevens . |
| 4,058,123 | 11/1977 | May ........................................ 604/131 |
| 4,112,932 | 9/1978 | Chirelli . |
| 4,180,068 | 12/1979 | Jacobsen et al. . |
| 4,187,849 | 2/1980 | Stim . |
| 4,233,982 | 11/1980 | Bauer et al. . |
| 4,240,411 | 12/1980 | Hosono . |
| 4,243,034 | 1/1981 | Brandt . |
| 4,338,934 | 7/1982 | Spademan . |
| 4,360,019 | 11/1982 | Portner et al. ........................... 604/131 |
| 4,424,833 | 1/1984 | Spector et al. . |
| 4,430,081 | 2/1984 | Timmermans . |
| 4,464,178 | 8/1984 | Dalton . |
| 4,475,548 | 10/1984 | Muto . |
| 4,512,766 | 4/1985 | Vailancourt . |
| 4,531,937 | 7/1985 | Yates . |
| 4,580,573 | 4/1986 | Quinn . |
| 4,601,710 | 7/1986 | Moll . |
| 4,610,665 | 9/1986 | Matsumoto et al. . |
| 4,610,710 | 9/1986 | Koontz . |
| 4,611,785 | 9/1986 | Steer . |
| 4,613,329 | 9/1986 | Bodicky . |

(List continued on next page.)

FOREIGN PATENT DOCUMENTS

| | | |
|---|---|---|
| 0113520 | 7/1984 | European Pat. Off. . |
| 0206553 | 5/1986 | European Pat. Off. . |
| 0223451 | 10/1986 | European Pat. Off. . |
| 0267584 | 5/1988 | European Pat. Off. . |
| 0312219 | 4/1989 | European Pat. Off. . |
| 0349955 | 7/1989 | European Pat. Off. . |
| 0350291 | 7/1989 | European Pat. Off. . |
| 0051718 | 5/1992 | European Pat. Off. . |
| 3042229 | 8/1980 | Germany . |
| 4020956 | 6/1990 | Germany . |

OTHER PUBLICATIONS

ENDOPATH RD3MM 3.5 mm Surgical Trocar Reducer (1991).

*Primary Examiner*—Paul J. Hirsch
*Attorney, Agent, or Firm*—Flehr, Hohbach, Test, Albritton & Herbert

[57] ABSTRACT

A portable infusion pump for infusing solutions from IV bags. The pump includes a housing having a compartment for removably receiving the bag in a solution-dispensing position. A push plate is mounted on the upper end of a flexible bladder having an outer wall which encloses a pressure chamber. The fluid is moved from a reservoir by a peristaltic pump into the pressure chamber so that the bladder is expanded to move the pressure plate toward the IV bag for dispensing the solution through IV tubing to the patient. The bladder has a predetermined configuration so that the differential volume required to fully dispense the solution from the IV bag is less than about 75% of the volume which is swept by movement of the push plate through its full stroke length. The IV tubing is connected to the IV bag by a filling spike having an annular groove which registers with a lock structure on the end of a lid. The lid is manually opened for insertion and removal of the bag to and from the housing compartment.

7 Claims, 4 Drawing Sheets

U.S. PATENT DOCUMENTS

| | | | |
|---|---|---|---|
| 4,626,243 | 12/1986 | Singh et al. | 604/141 |
| 4,626,245 | 12/1986 | Weinstein . | |
| 4,634,432 | 1/1987 | Kocak . | |
| 4,654,030 | 3/1987 | Moll et al. . | |
| 4,664,660 | 5/1987 | Goldberg et al. . | |
| 4,673,393 | 6/1987 | Suzuki et al. . | |
| 4,705,511 | 11/1987 | Kocak . | |
| 4,723,550 | 2/1988 | Bales et al. . | |
| 4,741,736 | 5/1988 | Brown | 604/134 |
| 4,758,225 | 6/1988 | Cox et al. . | |
| 4,817,631 | 4/1989 | Schnepp-Pesch et al. . | |
| 4,842,591 | 6/1989 | Luther . | |
| 4,857,062 | 8/1989 | Russell . | |
| 4,869,717 | 9/1989 | Adair . | |
| 4,874,378 | 10/1989 | Hillstead . | |
| 4,895,570 | 1/1990 | Larkin | 604/411 |
| 4,909,798 | 3/1990 | Fleischhacker et al. . | |
| 4,917,668 | 4/1990 | Haindl . | |
| 4,929,235 | 5/1990 | Merry et al. . | |
| 4,932,623 | 6/1990 | Johnson et al. . | |
| 4,938,259 | 7/1990 | Schmidt . | |
| 4,943,280 | 7/1990 | Lander . | |
| 4,960,412 | 10/1990 | Fink . | |
| 4,966,588 | 10/1990 | Rayman et al. . | |
| 4,978,341 | 12/1990 | Niederhauser . | |
| 5,000,745 | 3/1991 | Guest et al. . | |
| 5,002,557 | 3/1991 | Hasson . | |
| 5,017,059 | 5/1991 | Davis | 409/131 |
| 5,041,095 | 8/1991 | Littrell . | |
| 5,059,186 | 10/1991 | Yammamoto et al. . | |
| 5,071,413 | 12/1991 | Utterberg | 604/98 |
| 5,073,169 | 12/1991 | Raiken et al. . | |
| 5,082,429 | 1/1992 | Soderquist et al. | 604/153 |
| 5,103,854 | 4/1992 | Bailey et al. . | |
| 5,104,383 | 4/1992 | Shichman . | |
| 5,108,380 | 4/1992 | Herlitze et al. . | |
| 5,108,702 | 4/1992 | Hubner | 604/411 |
| 5,127,626 | 7/1992 | Hilal et al. . | |
| 5,137,520 | 8/1992 | Maxson et al. . | |
| 5,158,553 | 10/1992 | Berry et al. . | |
| 5,167,636 | 12/1992 | Clement . | |
| 5,207,645 | 5/1993 | Ross et al. | 604/141 |
| 5,207,714 | 4/1993 | Hayashi et al. . | |
| 5,209,736 | 5/1993 | Stephens et al. . | |
| 5,221,264 | 6/1993 | Wilk et al. . | |
| 5,226,891 | 7/1993 | Bushatz et al. . | |
| 5,242,412 | 9/1993 | Blake, III . | |
| 5,250,037 | 10/1993 | Bitdinger | 604/413 |
| 5,312,363 | 5/1994 | Ryan et al. . | |
| 5,330,431 | 7/1994 | Herskowitz | 604/153 |
| 5,334,164 | 8/1994 | Guy et al. . | |
| 5,342,315 | 8/1994 | Rowe et al. . | |
| 5,348,539 | 10/1994 | Herskowitz | 604/141 |
| 5,350,364 | 9/1994 | Stephens et al. . | |
| 5,352,201 | 10/1994 | Jemmott | 604/153 |
| 5,366,446 | 11/1994 | Tal et al. . | |
| 5,380,288 | 1/1995 | Hart et al. . | |
| 5,391,154 | 2/1995 | Young . | |
| 5,395,342 | 3/1995 | Yoon . | |
| 5,411,483 | 5/1995 | Loomas et al. . | |

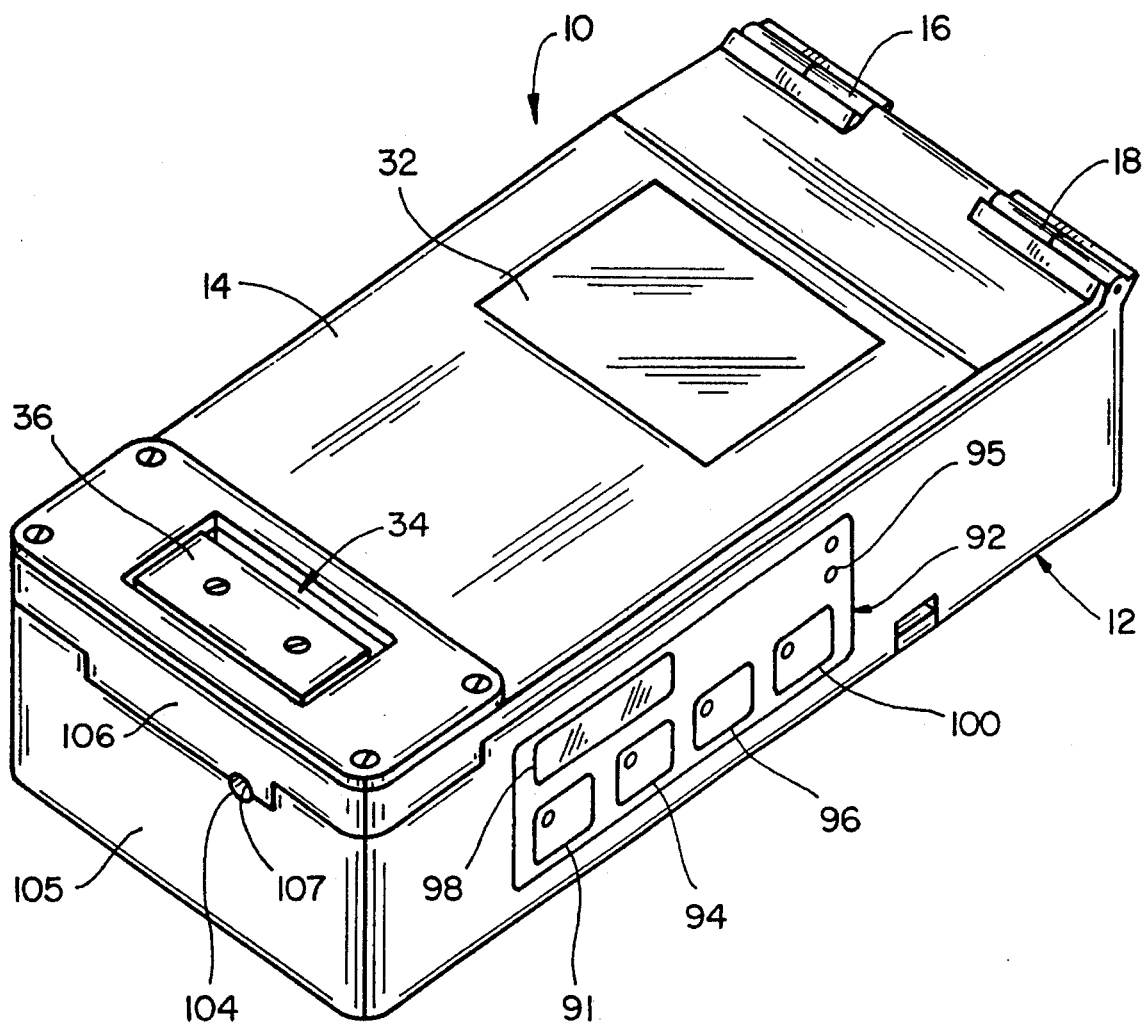
FIG_1
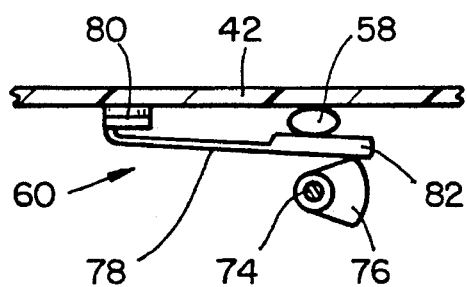
FIG_6

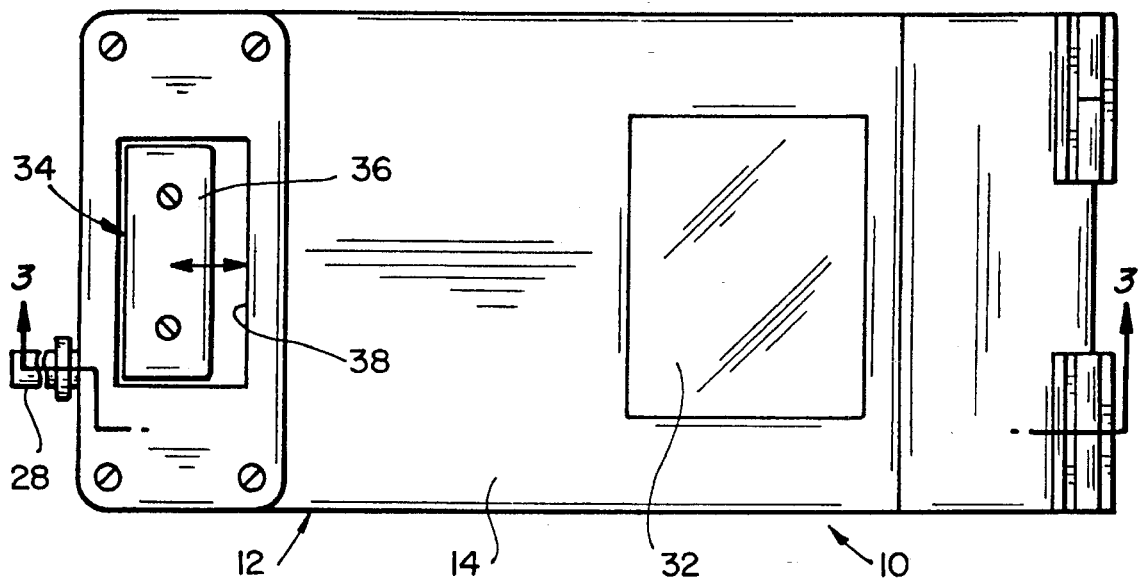
FIG_2
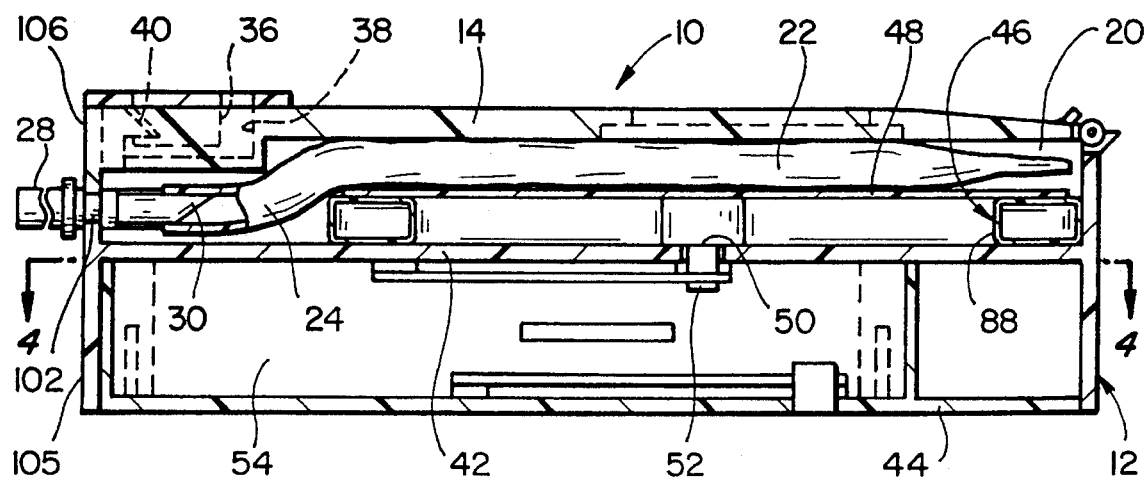
FIG_3

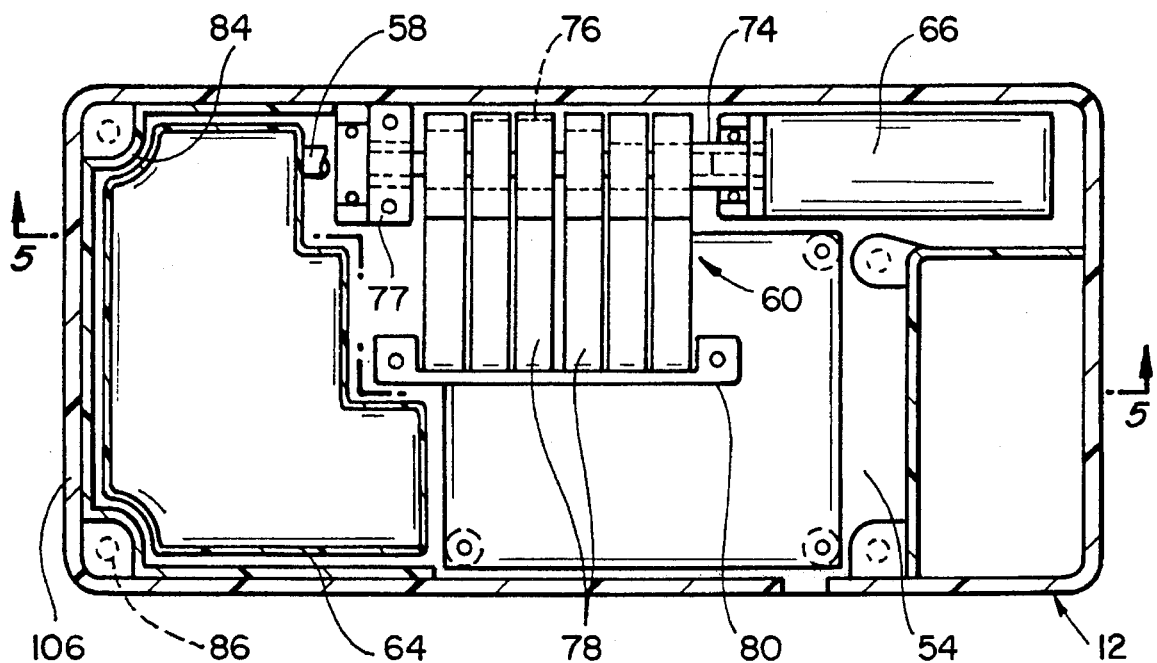
FIG_4
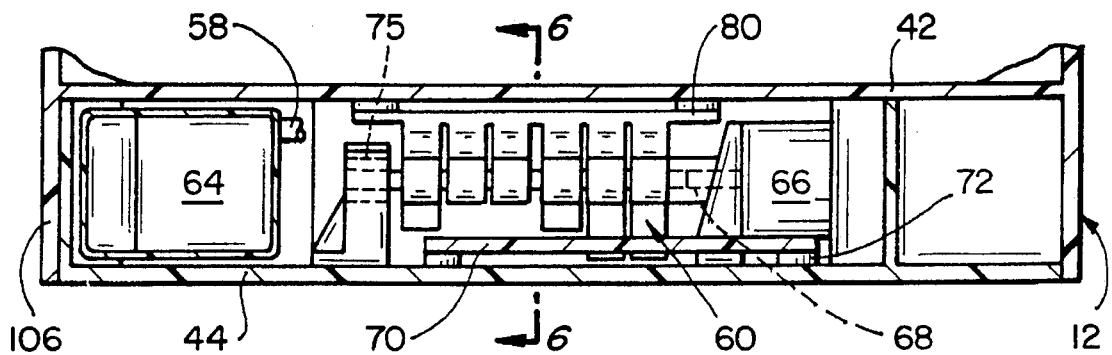
FIG_5

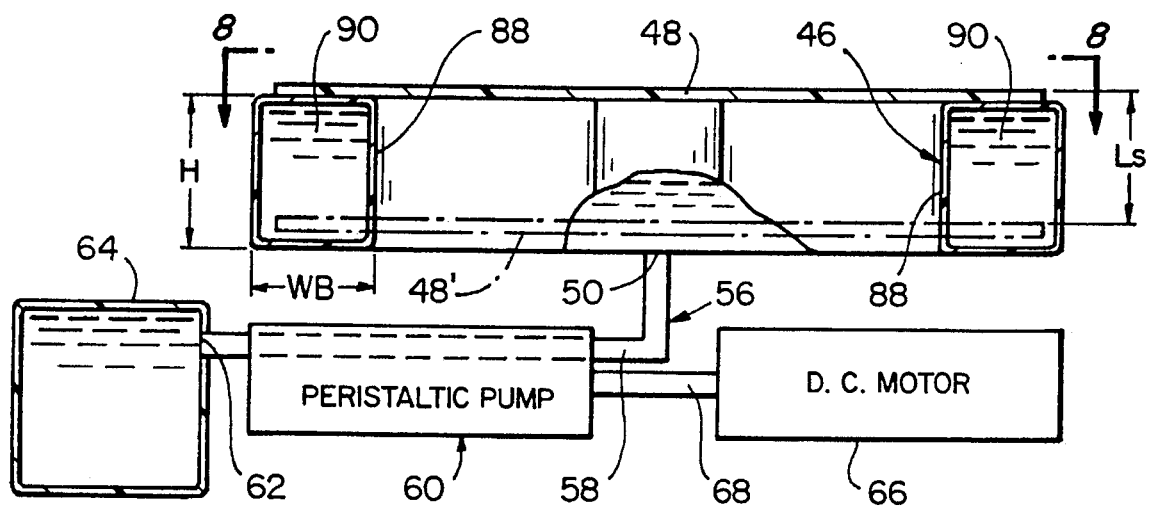
FIG_7
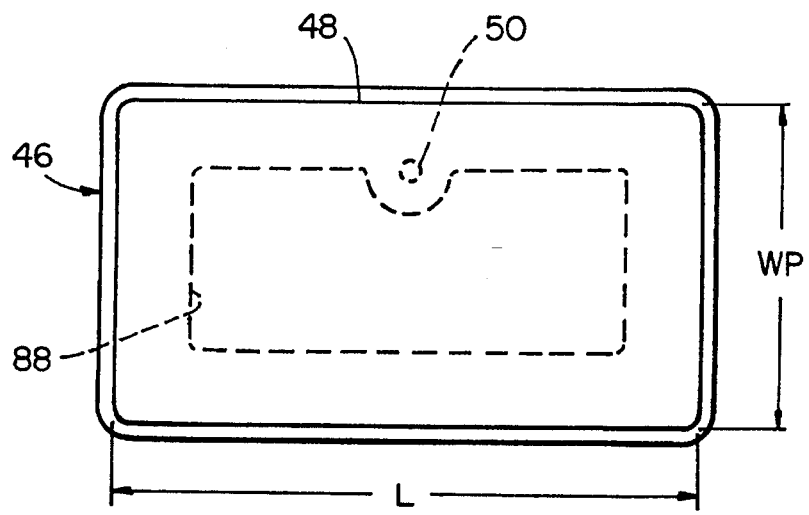
FIG_8

PORTABLE INFUSION PUMP

BACKGROUND OF THE INVENTION

1. Field of the Invention

This invention relates in general to the infusion of intravenous (IV) solutions. In particular, the invention relates to portable IV infusion pumps for use by ambulatory and other patients.

2. Description of the Related Art

Infusion pumps are used to deliver various types of solutions intravenously to patients. A variety of drugs are commonly administered to patients by means of the intravenous solutions. Among the types of therapies requiring this kind of administration are chemotherapy, antibiotic therapy and antiviral therapy. In many cases, patients receive multiple daily therapies. Certain medical conditions require infusions of drugs in solution over relatively short periods such as from 30 minutes to two hours. Infusion pumps have been developed in the prior art in an effort to meet these needs. There has been a requirement of providing portable infusion pumps for use by ambulatory patients and the like.

The different types of infusion pumps in the prior art include elastomeric pumps which squeeze the solution from flexible containers, such as balloons, into IV tubing for delivery to the patient. Spring-loaded pumps have also been provided to pressurize the solution containers or reservoirs. In certain pump designs cartridges containing flexible compartments that are squeezed by pressure rollers for discharging the solutions are provided, such as in U.S. Pat. No. 4,741,736. U.S. Pat. No. 5,330,431, issued to the inventor of the present invention, shows an infusion pump in which standard pre-filled single dosage IV bags are squeezed by the use of a roller. U.S. Pat. No. 5,348,539, also issued to the inventor of the present invention, shows an infusion pump in which prepackaged IV bags are squeezed by a bladder which is actuated by fluid pumped from a reservoir. In such a design, a relatively large volume of fluid must be pumped into the bladder to fully empty the IV bag. This requires a relatively larger sized pump and fluid reservoir, which results in a larger sized unit. The need has been recognized for an infusion pump which is smaller and more compact so that it can be better adapted for mobile use by ambulatory and other patients.

OBJECTS AND SUMMARY OF THE INVENTION

It is a general object of the invention to provide a new and improved portable infusion pump which is of smaller size and is more compact than conventional infusion pumps.

Another object is to provide a compact and portable infusion pump of the type described in which solutions from IV bags are infused by the action of inflatable bladders.

Another object is to provide an infusion pump of the type described in which a relatively small sized pump and fluid reservoir can be used for inflating a bladder to squeeze the IV bag for infusing the solution.

Another object is to provide an infusion pump of the type described having an improved arrangement for securely clamping the dispensing spike which interconnects IV tubing with the bag during the infusion process.

The invention in summary provides a portable infusion pump having a housing with a compartment which releasably receives an IV bag. For infusing solution from the bag, a push plate is moved by the expansion of a flexible bladder. Fluid is pumped from a reservoir into the bladder for inflating it. The bladder is shaped with a configuration such that the differential volume through which it expands to move the push plate through its stroke length is less than about 75% of the volume which is swept by movement of the push plate through its stroke during the infusion phase. Fluid is pumped in a reverse direction from the bladder to empty it and move the push plate back to its home position so that the spent IV bag can be removed from the compartment.

The foregoing and additional objects and features of the invention will appear from the following specification in which the several embodiments have been set forth in detail in conjunction with the accompanying drawings.

BRIEF DESCRIPTION OF THE DRAWINGS

FIG. 1 is a perspective view illustrating a portable infusion pump in accordance with one embodiment of the invention.

FIG. 2 is a top plan view of the infusion pump shown in FIG. 1.

FIG. 3 is a cross sectional view taken along the line 3—3 of FIG. 2.

FIG. 4 is a cross sectional view taken along the line 4—4 of FIG. 3.

FIG. 5 is cross sectional view taken along the line 5—5 of FIG. 4.

FIG. 6 is a fragmentary cross sectional view taken along the line 6—6 of FIG. 5.

FIG. 7 is a schematic view showing the interrelationship of certain components of the pump of FIG. 1.

FIG. 8 is a fragmentary top plan view to a reduced scale taken along the line 8—8 of FIG. 6.

DESCRIPTION OF THE PREFERRED EMBODIMENTS

In the drawings FIG. 1 illustrates generally at 10 a portable infusion pump according to a preferred embodiment of the invention. Infusion pump 10 provides an ambulatory system which enables health care professionals to infuse patients directly from single dose container bags which are pre-filled with IV solutions. Infusion pump 10 of the invention is suitable for use in homes, hospitals or clinics. It is readily adapted for operation in any position, such as resting on a table with the patient in bed, and it could also be carried by the patient.

Infusion pump 10 is comprised of a box-shaped housing 12 having a lid 14 which pivots open and closed about a pair of hinges 16, 18. With the lid in the closed position shown in FIG. 3, an internal elongate bag compartment 20 is formed below the lid for receiving the IV bag 22 in a solution-dispensing position. The typical IV bag is comprised of a flexible, transparent plastic container with side walls of generally rectangular shape. The bag has a front end molded with a pair of necks 24 (one of which is shown) which provide standard filling and dispensing ports. The dispensing port neck 24 is adapted to receive the pointed distal end of a dispensing spike 28. The proximal end 30 of the dispensing spike is adapted for connection with the end of standard IV tubing, not shown.

A transparent window pane 32 is fitted in an opening in the lid so that the health care professional can observe that the bag is in its proper solution-dispensing position when the lid is closed. A latch mechanism is provided to lock the lid in its closed position to prevent unintended removal of the IV bag before the infusion process is completed. The latch comprises a spring-loaded bar 36 which slides back and forth in a recess 38 at the front of the lid for releasably engaging a pointed detent 40 which is carried by the front end of housing 12.

A rigid divider plate 42, which can be of a suitable plastics material, is mounted horizontally within the housing approximately midway between housing bottom wall 44 and the top of lid. The top surface of the divider plate defines the bottom of bag compartment 20. Mounted on this top surface of the plate is a flexible bladder 46, which is best shown in FIGS. 3, 7 and 8. A horizontally flat push plate 48, which can be formed of a suitable rigid material such as ethylvinyl acetate (EVA) or acetybutylstyrene (ABS), is secured by suitable means such as adhesive across the top of the bladder. The upper surface of the push plate supports the IV bag in its solution-dispensing position. An inlet/outlet port 50 is formed in the bottom of the bladder, and this port connects with a fitting 52 which projects downwardly through an opening formed in divider plate 42. The distal end of fitting 52 extends into a lower compartment 54 which is formed between the divider plate and the housing lower wall. A flexible conduit 56 such as a length of silicone tubing is coupled at one of its ends with fitting 52. The conduit has a horizontal portion 58 (FIGS. 6 and 7) which extends through a peristaltic pump 60 that is mounted in the lower compartment. The opposite end of tubing portion 58 is connected with an inlet/outlet port 62 in a fluid reservoir 64, which is also mounted in the lower compartment. A DC motor 66 mounted in the lower compartment operates pump 60 by means of rotary drive shaft 68. The lower compartment also contains a suitable battery pack, not shown, which powers motor 66 as well as the electronics on a printed circuit board (PCB) 70.

PCB 70 is mounted within the lower compartment by means of mounting pads 72 which are secured to housing lower wall 44. The PCB mounts the electronic components which form a part of a suitable control circuit for operating the motor and other components of portable pump 10.

The construction and mode of operation of peristaltic pump 60 is shown in greater detail in FIGS. 4–6. The pump is comprised of a camshaft 74 having one end rotatably mounted within a suitable bearing 75 which is carried within a bracket 77 mounted above the housing bottom wall. The opposite end of the camshaft is coupled with motor drive shaft 68. Camshaft 74 is formed with a plurality, shown as six, of cam lobes 76 which are spaced apart at 60° incremental positions along the length of the shaft. A cam follower mechanism is provided which comprises a plurality of cantilever blades 78, equal in number to the number of cam lobes. The proximal ends of the cantilever blades are mounted by means of a bracket 80 to the lower surface of divider plate 42. The distal ends of the blades are formed with horizontally flat tips 82 which have lower surfaces that slidably engage the rotating surfaces of the cam lobes, as shown in FIG. 6.

The horizontal portion 58 of the tubing runs in a straight path in contact with the upper surfaces of the blade tips and the lower surface of the divider plate 42. As the camshaft is rotated by motor 66, a cycle of one rotation of each cam lobe causes its associated blade to compress against and flatten the underlying portion of the flexible tubing during a 60° phase and then release and permit the tubing to return to its circular shape during the remaining 300° phase. The combined action of the series of six cam lobes causes small volumes of fluid contained within the tube to be passed in waves along the length of the tubing in a direction which is dependent on the direction of rotation of the camshaft. Peristaltic pump 60 thereby enables reverse direction pumping by controlling the direction of rotation of the motor.

Preferably the fluid is pumped at a pressure in the range of 12–14 psi and is a low viscosity, non-toxic liquid such as oil, although other suitable liquids could be employed for this purpose. The invention also contemplates that a gaseous fluid such as carbon dioxide or air could be used to inflate bladder 46. In such case a suitable gas reservoir, pressure regulator and control valve (not shown) could be used, such as that described in connection with FIG. 12 of U.S. Pat. No. 5,348,539, the disclosure of which is incorporated herein by this reference.

Reservoir 64 is comprised of a flexible bag formed of a suitable plastics material such as EVA or PVC for containing a fluid volume of about 90 cc. As best shown in FIG. 4, reservoir 64 is shaped to economize space within lower compartment 54 by conforming with the shapes of bearing bracket 78, the bracket 80 for holding the cam follower blades, and vertical posts 84 which accommodate bolts 86 that are provided to assemble bottom wall 44 to the housing.

Bladder 46 is comprised of a flexible outer wall 88 formed of a suitable plastics material such as PVC. The outer wall encloses a pressure chamber 90 for receiving a charge of fluid which is moved by the peristaltic pump through inlet/outlet port 50. When the pressure chamber within the bladder is being filled with fluid the bladder expands and pushes pressure plate 48 upwardly. The plate is moved by the bladder through the full stroke length $L_S$ from the fully collapsed position shown at 48' to the fully extended position shown in solid line in FIG. 7. Pressure plate 48 has a width WP and length L, the product of which defines an area $A_1$. The volume $V_1$ which is swept by movement of the push plate through its stroke length is $V_1 = L_S \times A_1$.

Bladder 46 is shaped with a configuration such that the differential volume $V_2$ through which the bladder expands to fully extend the push plate is less than about 75% of the volume $V_1$. In the illustrated embodiment, this configuration of bladder 46 is a torus in which the cross section of each of the four sides has a height H of 0.75" and width WB of 0.45", as shown for the left side of the torus when viewed in FIG. 8. With the length along the long axis of the torus being 5.05", and the width along the short axis of the torus being 3.00", and with an outer wall thickness of 0.10", then an 80 cc charge of fluid fills pressure chamber 90 to actuate the bladder to its fully extended position. In this example $V_2$=80 cc and $V_1$=167 cc so that $V_2$ is 48% of $V_1$. This is in comparison to the prior art IV pumps employing rectangular shaped bladders which require fluid volumes on the order of 115 cc or more to infuse both large (115 cc) and small (50 cc) IV bags. In such prior art pumps the amount of fluid required to pump the bladder sufficient to fully dispense solution from the bags is about the same as the volume of a large IV bag. With the bladder configured in the manner of the present invention the sizes of the bladder and reservoir can be kept to a minimum, and the size of the pump and motor can also be minimized, so that infusion pump 10 can be smaller and more compact for ease of portability. For example, certain prior art infusion devices provide pumps which comprise a pair of spaced rotors operated by intermeshing gears with the rotors each having 1½" diameters. In comparison, the peristaltic pump of the present invention has a diameter on the order of 1" for providing the requisite pumping action. In the environment of a compact infusion pump, this 0.5" difference in size is significant.

While in the illustrated embodiment the bladder configuration which provides the relationship $V_2 \leq 0.75 \times V_1$ is a torus, other configurations providing this relationship could be employed. For example, the bladder in plan view could be shaped as the letters "H", an "I", an "O", an "E", an "X" or the number "8" or other similar configuration which provides this relationship.

A suitable control circuit, not shown, which incorporates PCB 70 is provided for controlling the peristaltic pump through its operating cycle. The control circuit could incorporate certain elements and steps of the control arrangement and method described in connection with FIGS. 10–11 of U.S. Pat. No. 5,348,539, which is incorporated herein by this reference. In the broad aspects of the method of operation, pump 10 is turned on by manually pushing POWER switch 91 which is a part of the control panel 92 on one side of housing 12. Suitable sensors, not shown, can be provided as a part of the control circuit to sense closure of lid 14, pressure levels in bladder 46 and battery charge. The infusion process is initiated by manually pressing the INFUSE switch 94 which turns motor 66 on so that it rotates camshaft 68 in a direction which peristaltically pumps fluid from reservoir 64 through tubing 58 into pressure chamber 90 of the bladder. During the infusion phase the CHECK STATUS indicator light 94 on panel is off. Should there be an obstruction in the tubing causing an overpressure condition in the bladder, or upon completion of the infusion phase, then the CHECK STATUS light will turn on as a warning or alert to the health care professional. At any time during the infusion process, the PAUSE switch 96 on the panel can be pressed to temporarily stop the infusion process. The power is automatically turned off if the infusion is not started within a five minute period.

A suitable pressure sensing switch, not shown, of the type described in connection with FIG. 9 of U.S. Pat. No. 5,348,539, can be provided to sense the back pressure within bladder pressure chamber 90. When this pressure reaches a predetermined level for a defined length of time indicating that solution in the IV bag has been fully dispensed, the circuit turns the motor off to stop the pumping action. During this infusion phase of the cycle the infusion time is shown by the digital readout 98 on the panel. After infusion is completed, RESET switch 100 is pressed. The control circuit then rotates the motor in a reverse direction and operates the peristaltic pump so that it pumps fluid out of bladder 46 and back into reservoir 64. As fluid is pumped out of the bladder it will collapse downwardly due to atmospheric pressure and pull push plate 48 downwardly and away from the IV bag to position 48' shown in FIG. 7. When a predetermined low or negative pressure is sensed within the bladder pressure chamber, the circuit turns the motor off. Lid latch 36 can then be released to permit the health care professional to open the lid and remove the spent IV bag.

As best shown in FIG. 3, dispensing spike 28 is formed about its proximal end with an annular groove 102. The annular recessed portion within the groove releasably fits on its lower side into a matching U-shaped seat 104 (FIG. 1) that is formed on the upper edge of housing end wall 105. The front end 106 of the lid is also formed with a U-shaped seat 107 which moves into register with and fits into the top side of spike groove 102 when the lid is closed. This locks the spike against unintended removal from the housing during the infusion process.

While the foregoing embodiments are at present considered to be preferred it is understood that numerous variations and modifications may be made therein by those skilled in the art and it is intended to cover in the appended claims all such variations and modifications as fall within the true spirit and scope of the invention.

What is claimed is:

1. A portable infusion pump for infusing intravenous solution from a bag through tubing into a patient, the bag having a flexible sidewall which at least partially encloses a volume to contain the solution, the bag further having a dispensing port for releasable connection with an end of the tubing, the pump comprising the combination of a housing having a compartment for removably receiving and supporting the bag in a solution-dispensing position, a push plate positioned within the housing, said push plate having a planar area $A_1$ which is in juxtaposed relationship with said flexible sidewall when the bag is in said solution-dispensing position, actuating means for moving the push plate against said flexible sidewall for compressing the bag and discharging solution therefrom during an infusion phase of an operating cycle, said push plate being moved by the actuating means from a home position toward the bag through a predetermined stroke length $L_S$ which is sufficient to substantially empty the solution from the bag with the volume $V_1$ which is swept by movement of the push plate through its stroke length having the relationship $V_1 = L_S \times A_1$, said actuating means comprising 1) a reservoir having a supply chamber for holding a supply of fluid, 2) a flexible bladder having an outer wall which encloses a pressure chamber for receiving a charge of said fluid, said outer wall being expandable from a non-operating position through a differential volume $V_2$ which is sufficient to act against and move said push plate through said length $L_S$, said bladder being shaped with a configuration by which said volume $V_2$ is less than about 75% of the volume $V_1$, and 3) pump means for pumping fluid between the reservoir and pressure chamber, said pump means being operable for pressurizing the fluid within the pressure chamber of the bladder to a pressure which is sufficient to expand the outer wall through said differential volume $V_2$.

2. A pump as in claim 1 in which said configuration of the bladder comprises a torus.

3. A pump as in claim 1 which includes means comprising a flexible conduit for directing fluid between the reservoir and pressure chamber, and said pump means comprises a peristaltic pump operable in an infusion phase for successively compressing portions of the conduit and moving the fluid in waves within the conduit from the reservoir into the pressure chamber, said pump means including a motor having the drive shaft, and said peristaltic pump comprises a rotor and means for coaxially mounting said rotor with said drive shaft.

4. A pump as in claim 3 in which said pump is operable in a reset phase for moving the fluid in waves from the pressure chamber into the reservoir and for moving the push plate from the bag toward said home position.

5. A pump as in claim 1 in which said fluid comprises an hydraulic fluid.

6. A pump as in claim 1 for use with intravenous tubing having a dispensing spike connected with said end of the tubing, said dispensing spike having an annular groove together with an outlet end positioned distally of the groove for connection with said dispensing port of the bag, said pump further being characterized in that said housing comprises a structure positioned in register with said annular groove when the outlet end of the spike is connected with the dispensing port, and means for moving said structure into and out of lockable relationship with said annular groove.

7. A pump as in claim 6 in which said means for moving the structure comprises a lid mounted on the housing for movement between open and closed positions for enabling insertion and removal of the bag into and from said compartment, and groove-engaging means on the lid for supporting the structure for movement into and out of said lockable relationship with the annular groove responsive to the lid being moved to the respective closed and open positions.

* * * * *